United States Patent [19]

Vailancourt

[11] Patent Number: 4,722,731

[45] Date of Patent: Feb. 2, 1988

[54] AIR CHECK VALVE

[76] Inventor: Vincent L. Vailancourt, 14 Bunyan Dr., Livingston, N.J. 07039

[21] Appl. No.: 924,853

[22] Filed: Oct. 28, 1986

Related U.S. Application Data

[63] Continuation of Ser. No. 720,734, Apr. 8, 1985, abandoned.

[51] Int. Cl.⁴ ............................................. A61M 5/00
[52] U.S. Cl. ................................... 604/122; 137/860; 604/129
[58] Field of Search ..................... 604/6, 9, 10, 30, 31, 604/34, 118, 122, 123, 246, 247, 323, 129; 128/DIG. 12; 137/512.3, 493, 860; 251/5

[56] References Cited

U.S. PATENT DOCUMENTS

| | | | |
|---|---|---|---|
| 2,988,103 | 6/1961 | Canvasser | 251/5 |
| 3,298,391 | 1/1967 | Savage | 251/5 |
| 3,445,085 | 5/1968 | Eckel et al. | 251/5 |
| 3,991,768 | 11/1976 | Portnoy | 251/5 |
| 4,258,712 | 3/1981 | Harms et al. | 604/122 |
| 4,313,462 | 2/1982 | Adamson | 137/512.3 |
| 4,515,589 | 5/1985 | Austin et al. | 604/122 |
| 4,552,553 | 11/1985 | Schulte et al. | 604/9 |
| 4,568,333 | 2/1986 | Sawyer et al. | 604/122 |
| 4,592,747 | 6/1986 | Pool | 604/246 |

FOREIGN PATENT DOCUMENTS 2513490  3/1974  Fed. Rep. of Germany .......... 604/5

Primary Examiner—Stephen C. Pellegrino
Attorney, Agent, or Firm—Kenyon & Kenyon

[57] ABSTRACT

The air check valve has a one-piece housing provided with a pair of coaxial passageways and radiating ports which are closed over by an elastic sleeve. When the pressure in the upstream passageway is greater than in the downstream passageway and the crack or opening pressure of the sleeve is exceeded, the sleeve expands radially so as to permit communication between the two passageways for the conveyance of fluid.

The air check valve may also be provided with a one-way valve in a partition between the two passageways to permit withdrawal of fluids from a patient.

18 Claims, 7 Drawing Figures

AIR CHECK VALVE

This is a continuation of application Ser. No. 720,734 filed Apr. 8, 1985, now abandoned.

This invention relates to an air check valve. More particularly, this invention relates to an air check valve for use with intravenous lines.

As is known, with the introduction of concentrated hyperalimentation solutions, a need has arisen to access a major vein where there is high blood flow. However, one potential problem which is associated with central line placement concerns the physiological fact that blood in a major vein, such as the superior vena cava is under negative pressure. Hence, should an intravenous line connected to a central venous catheter become accidently disconnected or should the line run dry and be vented to the outside environment, then air might flow through the catheter into the major vein. This can lead to an air embolism with potential fatal results.

In the past, one means to prevent air ingress is to place a hydrophilic filter in the line just prior to the catheter. However, this is expensive and does not provide protection should a final connection between the catheter and filter open. Also, catheters which are presently in use frequently have two, three, four or more lines. Thus, to place a filter in each line would be extremely expensive and cumbersome amongst other considerations.

Accordingly, it is an object of the invention to provide a positive means for preventing air ingress in an automatic manner into an intravenous line.

It is another object of the invention to provide a relatively simple air check valve to preclude passage of air therethrough.

It is another object of the invention to provide a relatively inexpensive air check valve which can be readily manufactured.

It is another object of the invention to provide an air check valve which is made of a minimum of parts.

Briefly, the invention provides an air check valve which is constructed of a one-piece housing in which a pair of spaced apart passageways are located at opposite ends with at least one port extending radially of and from each passageway and an elastic sleeve which is disposed over the housing with an interference fit concentrically of the ports in order to seal the ports relative to each other. The interference fit is sufficient to permit radial expansion of the sleeve under a predetermined pressure in one of the passageways for the passage of a fluid under pressure from the port in that passageway to the port of the other passageway.

With the housing of tubular shape, for example in the form of a cylinder, the two passageways may be coaxial. In this case, one passageway may be connected with a central venous catheter line for delivering intravenous fluid to a patient while the other passageway is connected to an intravenous line for delivering a flow of intravenous fluid to the catheter line. The construction is such that under conditions of no flow, i.e. at zero static pressure in the intravenous line, the elastic sleeve seals off the ports so that no air may flow between the two lines via the air check valve. However, when the intravenous fluid flows in the intravenous line and the pressure exceeds the crack or opening pressure of the sleeve, for example about one to four inches of water, the sleeve lifts, i.e. radially expands, so as to communicate the ports of the respective passageways with each other. In this way, flow passes from one passageway through the annular space between the sleeve and the housing and exits through the other passageway into the catheter line. When the fluid flow stops, the sleeve relaxes back to the original position closing off the ports and respective passageways from each other.

In order to facilitate the mounting and operation of the sleeve, the housing may be provided with a pair of annular shoulders to define an annular groove therebetween and to permit mounting of the sleeve on the shoulders with the intermediate portion of the sleeve contracted within the groove in sealing relation to the ports. To this end, the ends of the sleeve may be adhesively secured onto the shoulders to form a fixed connection therebetween.

In addition, the valve may be provided with a support tube which is mounted on the housing concentric to and about the sleeve in order to limit radial expansion of the sleeve. The support tube also serves to protect the elastic sleeve against damage.

Where made of plastic material, the housing can be readily molded. For assembly purposes, the sleeve can then be fitted about the housing and secured to the annular shoulders in bridging relation to the ports from the passageways. Thereafter, the support tube can be slid onto the housing to protect the sleeve.

Should the specific fluid flow line require that fluid be withdrawn from a patient, the air check valve can be provided with a partition between the two passageways and a one way valve in the partition which is able to communicate the passageways with each other in response to a higher pressure in the line connected to the patient.

These and other objects and advantages of the invention will become more apparent from the following detailed description taken in conjunction with the accompanying drawings wherein:

FIG. 6 illustrates an enlarged view of the one-way valve in a closed position in accordance with the invention; and FIG. 7 illustrates an enlarged view of the one-way valve in an opened condition.

Figure 1:
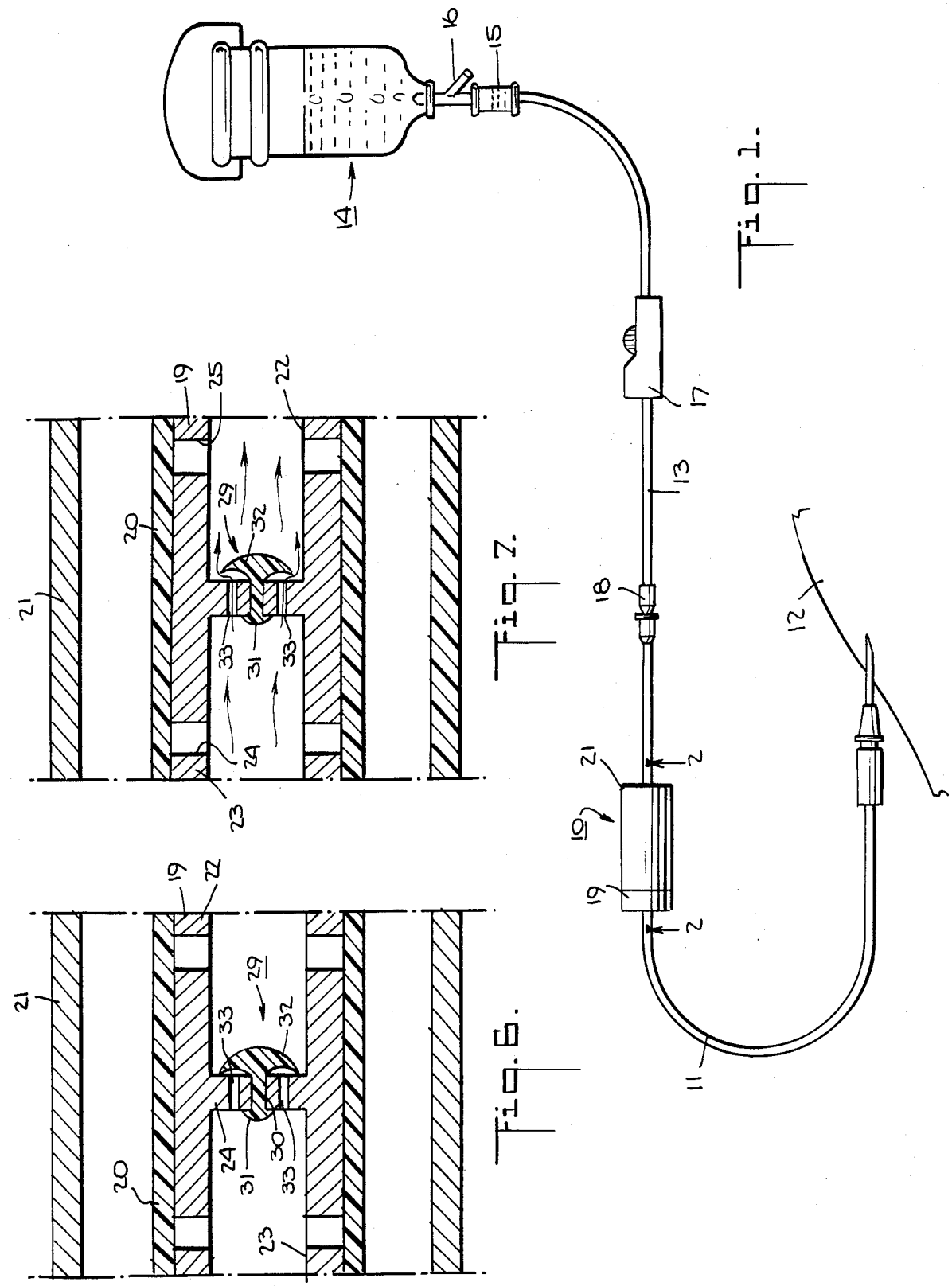
FIG. 1 illustrates an air check valve according to the invention and placed between a catheter line and an intravenous fluid source.

Referring to FIG. 1, the air check valve 10 is disposed between a central venous catheter line 11 for delivering intravenous fluid to a patient 12 and an intravenous line 13 which is connected to a source 14 of intravenous fluid, such as an IV bottle. As indicated, a drip chamber 15 of known construction may also be provided between the bottle 14 and the intravenous line 13. An air vent 16 allows IV fluids to flow from the bottle 14 by venting external air into the bottle 14 (fluid displacement). A suitable means such as a roller clamp 17 may be provided in the intravenous line 13 in order to stop the flow of fluid in the line 13 when desired. A connection 18, such as a conventional male to female luer fitting, serves to connect the IV administration set to the catheter line 11.

Figure 2:
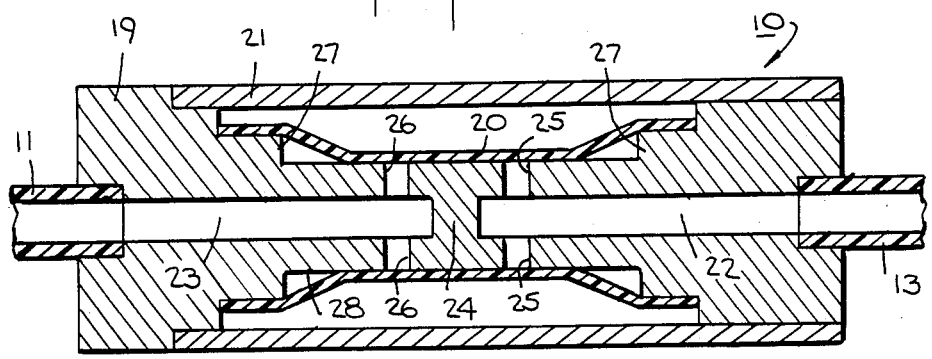
FIG. 2 illustrates a cross sectional view of the air check valve taken on line 2—2 of FIG. 1 in a closed condition.

Referring to FIG. 2, the air check valve 10 is formed of a one piece housing 19, an elastic sleeve 20 and a support tube 21.

The one piece housing 19 is of tubular construction having a cylindrical cross-sectional shape and is provided with a pair of spaced apart coaxial passageways 22, 23 which are separated from each other by a centrally disposed partition 24. As indicated, one passageway 22 communicates directly with the intravenous line 13 for receiving a flow of fluid therefrom while the opposite passageway 23 communicates directly with the catheter line 11 so as to deliver the fluid thereto.

A plurality of ports 25 extend radially of and from the upstream passageway 22 to the exterior of the housing 19 while a similar number of ports 26 extend radially from the downstream passageway 23 to the exterior of the housing 19. As shown in FIG. 2, the housing 19 also has a pair of annular shoulders 27 which define an annular groove 28 therebetween which communicates with the ports 25, 26 which extend from the passageways 22, 23.

The elastic sleeve 20 is disposed at the ends circumferentially about each shoulder 27 and is secured thereto, for example by an adhesive. In addition, the sleeve 20 which is externally unpressurized has an interference fit (i.e., is pre-stressed) concentrically of the reduced section of the housing 19 formed by the groove 28 so as to seal the ports 25, 26 relative to each other. This interference fit is sufficient to permit radial expansion of the sleeve 20 under a predetermined pressure in the passageway 22 for passage of the intravenous fluid under pressure from the ports 25 to the ports 26 of the other passageway 23, for example as indicated in FIG. 3.

Figure 3:
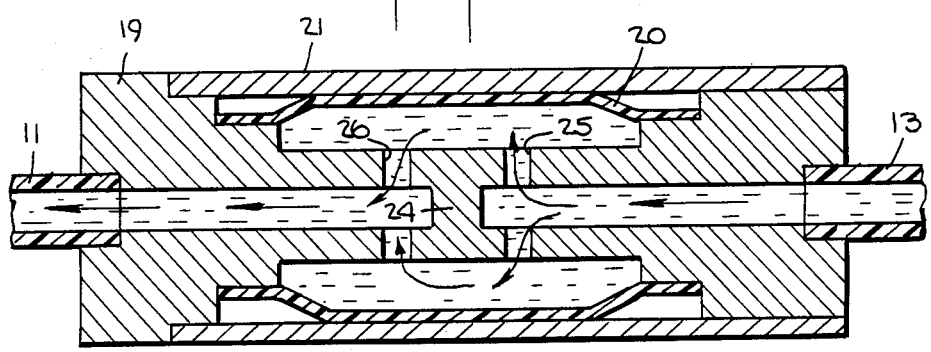
FIG. 3 illustrates a view similar to FIG. 2 with the valve in an opened condition.

The support tube 21 is mounted on the housing 19 concentrically about the sleeve 20 in order to limit expansion of the sleeve 20 as indicated in FIG. 3. In this regard, the support tube 21 also serves to protect the sleeve 20 externally from damage.

The housing 19 and support tube 21 may be made of any suitable material, such as a plastic material which can be readily molded. Further, the cross sectional shape of the housing 19 and support tube 21 may be other than circular.

The elastic sleeve 20 may be made of any suitable material which is capable of forming an effective seal between the respective sets of ports 25, 26 while being radially expandable under a predetermined pressure.

Referring to FIG. 2, with no pressure in the intravenous line 13, the valve 10 is in the closed position as indicated. In this position, the sleeve 20 is constricted within the annular groove 28 in seal-tight relation over the radially outer ends of the ports 25, 26. Should a pressure develop in the intravenous line 13, for example due to opening of the clamp 17 (see. FIG. 1) fluid is delivered into the upstream passageway 22 and passes through the ports 25 radially against the elastic sleeve 20. When the pressure exceeds the crack or opening pressure of the sleeve 20, for example about one to four inches of water, the sleeve 20 radially expands as indicated in FIG. 3 to permit the fluid to flow from the ports 25 into the ports 26 leading to the downstream passageway 23. As indicated in FIG. 3, the fluid also fills an annular chamber then existing between the sleeve 20 and the housing 19. The fluid flow exits from the passageway 23 into the catheter line 11 so as to be delivered to the patient 12 (see FIG. 1).

Figure 4:
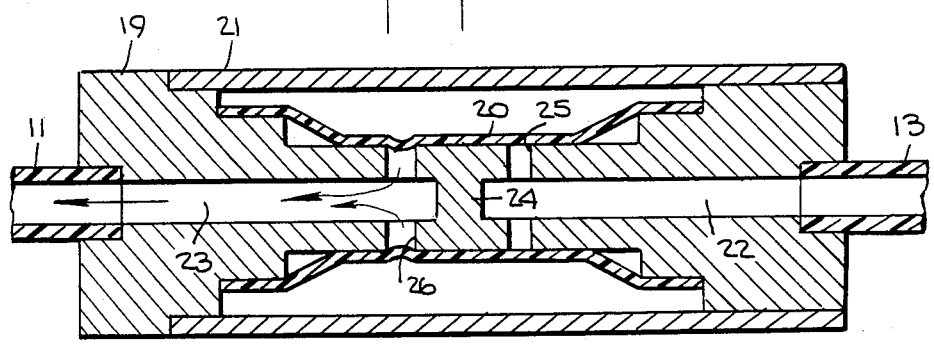
FIG. 4 illustrates a view of the valve in a closed position with a negative pressure on the downstream side.

When the flow in the intravenous line 13 is shut off, the pressure in the passageway 22 will decrease so that the sleeve 11 contracts radially about the reduced portion of the housing 19 to again close off the sets of ports 25, 26 from each other. As indicated in FIG. 4, should a negative pressure exist within the catheter line 11, for example due to a negative pressure in a vein in the patient 12, the sleeve 20 deforms slightly into each port 26. Thus, the negative pressure in the catheter line 11 also serves to maintain a seal between the passageways 22, 23.

The air check valve 10 may be of any suitable size depending upon the use for which the valve is intended. Generally, the valve is of a small size which can be incorporated into any fluid line for intravenous therapy. For example, for a flow rate of about 100 cc/minute under about three feet of water head, the diameter of the valve 10 is about 0.250 inches with the diameter of the passageways 22, 23 about 0.090 inches. In this case, the valve is suitably sized to connect with various types of intravenous lines which are generally of an internal diameter of between 0.080 inches to 0.125 inches with external diameters of between ⅛ inch to 3/16 inch. For these sizes, the crack pressure for opening the valve 10 is about two inches head of water. Further, the radial ports 25, 26 may be of any suitable size depending upon the flow and the crack pressure of the sleeve. For example, ports of a diameter of 1/16 inch may be used to give a crack pressure of 8 inches of water.

The sleeve 20 in a relaxed state has a diameter which is slightly less than the diameter of the reduced portion of the housing 19 within the annular groove 28 so as to provide the necessary interference fit for sealing purposes.

The maximum flow rate through the valve is determined by the number and size of the ports 25, 26.

Figure 5:
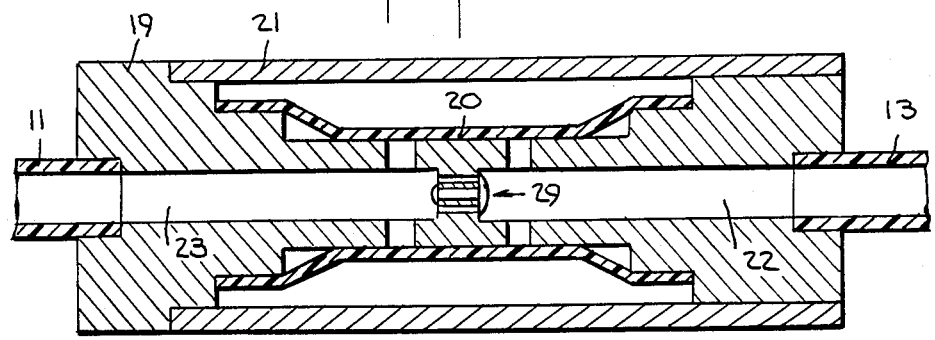
FIG. 5 illustrates a modified air check valve employing a one-way valve between the passageways therein.

Referring to FIG. 5, wherein like reference characters indicate like parts above, the valve 10 may be constructed to permit fluids to be withdrawn from a patient. In this regard, a one-way valve 29 is disposed in the partition 24 between the passageways 22, 23. As indicated in FIGS. 5 and 6, this one-way valve 24 is in the form of a one-piece umbrella valve of plastic material with a stem 30 which passes through the partition 24, a stop 31 at one end and an enlarged cap 32 at the opposite end. The cap 32 is sized to fit over one or more ports 33 extending through the partition 24 to communicate the passageways 22, 23 with each other.

When the pressure in the passageway 22 is greater than in the passageway 23, the umbrella valve 29 is in the position shown in FIG. 6 with the cap 32 covering over the ports 33 in sealed manner. Should the pressure in the passageway 23 become greater than the pressure in the passageway 22, the umbrella valve 24 shifts into the position illustrated in FIG. 7 so that the ports 33 communicate the passageway 23 with the passageway 22. At this time, fluid in the passageway 23 flows into the passageway 22 as indicated by the arrows.

The invention thus provides an air check valve in which the risk of air passing into a catheter line from an intravenous line is reduced. Further, the air check valve does not require any filter such as a hydrophilic filter so that drug binding can be eliminated. Further, the air check valve may be used with any type of connector in order to convey fluid therethrough.

The invention further provides an air check valve which is easy to make and which is of economical construction.

Further, since the air check valve is made of a minimum of parts, assembly can be performed in a relatively simple manner. Also, if cleaning or repair is required, the parts can be readily separated for this purpose.

The air check valve may be used in any suitable type of environment, for example for feeding intravenous fluids into a patient, for expelling fluids from a patient, and the like. For example, in the case where fluids are to be voided from a bladder to a pedestrian bag, the air check valve can be used to preclude infection by forming a stop between the waste fluid collected in the bag and any fluid in a line leading to the bladder. In this respect, the valve would be constructed to open under the pressure generated by the fluid voided from the bladder. Furthermore, the groove 28 between the shoulders 27 of the housing 19 may be provided with an oligodynamic coating which would be contacted by the elastic sleeve 20 upon closing in order to sterilize any urine or like fluid which may remain trapped between the sleeve 20 and the housing groove 28. Of course, any other suitable antiseptic coating might also be used.

What is claimed is:

1. An air check valve comprising
a housing having a reduced section, a pair of spaced apart coaxial passageways and at least one port extending radially of and from each respective passageway within said reduced section; and
an externally unpressurized elastic sleeve disposed on said housing and constricted into said reduced section with an interference fit concentrically of said ports to seal said ports relative to each other, said interference fit being sufficient to permit radial expansion of said sleeve under a predetermined pressure in one of said passageways to allow communication between said ports for passage of a fluid under pressure from said one passageway to the other of said passageways.

2. An air check valve as set forth in claim 1 which further comprises a one way valve in said partition for communicating said other passageway with said one passageway in response to a predetermined differential pressure therebetween.

3. An air check valve as set forth in claim 2 wherein said one-way valve is an umbrella valve.

4. In combination
a central venous catheter line for delivering intravenous fluid to a patient;
an intravenous line for delivering a flow of intravenous fluid to said catheter line; and
an air check valve between said lines, said valve including a one-piece housing having a reduced section, a first passageway in said housing connected to said intravenous line to receive a flow of fluid therefrom under pressure, a plurality of ports communicating with and extending radially from said passageway within said reduced section, a second passageway in said housing connected to said catheter line to deliver intravenous fluid thereto, a plurality of ports communicating with and extending radially from said second passageway within said reduced section, a partition separating said passageways and an externally unpressurized elastic sleeve constricted into said reduced section and disposed over said ports with an interference fit sufficient to permit radial expansion of said sleeve under a predetermined pressure to communicate said ports of said passageways with each other via an annular chamber then existing between said sleeve and said housing for passage of the intravenous fluid to said catheter line.

5. The combination as set forth in claim 4 wherein said valve includes a support tube mounted on said housing concentric to and spaced about said sleeve.

6. The combination as set forth in claim 5 wherein said housing and said tube are of cylindrical shape.

7. The combination as set forth in claim 4 which further includes an oligodynamic coating on said housing between said housing and said sleeve.

8. The combination as set forth in claim 4 wherein said pressure is about one to four inches of water.

9. The combination of claim 4 wherein said valve is sized for a flow rate of about 100 cc/minute under about three feet of water head.

10. The combination of claim 4 wherein each passageway has a diameter of about 0.090 inches.

11. The combination of claim 10 wherein said pressure is about two inches head of water.

12. An air check valve for a venous catheter line comprising
a housing having a pair of spaced apart coaxial passageways with one of said passageways being sized to connect with the catheter line, a partition separating said passageways, a reduced section and a plurality of ports extending radially within said reduced section and from each respective passageway; and
an externally unpressurized elastic sleeve disposed on and about said housing and constricted into said reduced section with an interference fit concentrically of said ports to seal said ports relative to each other, said interference fit being sufficient to permit radial expansion of said sleeve under a predetermined pressure in the other of said passageways to allow communication between said ports for passage of a fluid under pressure from said other passageway to an annular chamber then existing between said sleeve and said housing and then to said one passageway.

13. An air check valve as set forth in claim 12 which further includes a support tube mounted on said housing concentric to and about said sleeve.

14. An air check valve as set forth in claim 12 wherein said housing includes a pair of annular shoulders defining an annular groove therebetween, said groove being in communication with said ports and said sleeve being sealingly secured at opposite ends to said shoulders and being constricted intermediately thereof in said groove.

15. An air check valve as set forth in claim 12 wherein said predetermined pressure is about one to four inches of water.

16. An air check valve for a venous catheter line comprising
a housing having a pair of spaced apart coaxial passageways with one of said passageways being sized to connect with the catheter line, a partition separating said passageways, a pair of annular shoulders defining an annular groove therebetween and a plurality of ports extending radially and from each respective passageway to said annular groove; and
an externally unpressurized elastic sleeve mounted on said shoulders and constricted into said groove with an interference fit concentrically of said groove to seal said ports from each other, said interference fit being sufficient to permit radial expansion of said sleeve under a predetermined pressure in the other of said passageways for passage of an intravenous fluid under pressure from said other passageway through at least one of said ports to an annular chamber then existing between said sleeve and said housing and then to said one passageway through at least another one of said ports.

17. An air check valve as set forth in claim 16 which further comprises a one way valve in said partition for communicating said passageways with each other in response to a predetermined differential pressure therebetween.

18. An air check valve as set forth in claim 17 wherein said one-way valve is an umbrella valve.

* * * * *